(12) United States Patent  
Dillard et al.

(10) Patent No.: US 6,578,431 B2  
(45) Date of Patent: Jun. 17, 2003

(54) METHOD AND APPARATUS FOR DETERMINING BULK MATERIAL PROPERTIES OF ELASTOMERIC MATERIALS

(75) Inventors: David A. Dillard, Blacksburg, VA (US); Didier Lefebvre, Mundelein, IL (US); Jang-Horng Yu, Blacksburg, VA (US)

(73) Assignee: Virginia Tech Intellectual Properties, Inc., Blacksbury, VA (US)

( * ) Notice: Subject to any disclaimer, the term of this patent is extended or adjusted under 35 U.S.C. 154(b) by 0 days.

(21) Appl. No.: 09/824,581

(22) Filed: Apr. 3, 2001

(65) Prior Publication Data

US 2001/0049967 A1 Dec. 13, 2001

Related U.S. Application Data

(60) Provisional application No. 60/194,400, filed on Apr. 4, 2000.

(51) Int. Cl.[7] ................................................. G01N 3/08  
(52) U.S. Cl. ........................................................ 73/819  
(58) Field of Search .......................... 73/788, 790, 804, 73/807, 818, 819

(56) References Cited

U.S. PATENT DOCUMENTS

| | | | | |
|---|---|---|---|---|
| 3,589,166 A | * | 6/1971 | Klar et al. | 374/49 |
| 4,633,718 A | * | 1/1987 | van Engelshoven | 73/822 |
| 5,916,664 A | * | 6/1999 | Rudy | 2/161.1 |
| 6,089,106 A | * | 7/2000 | Patel et al. | 177/144 |
| 6,191,414 B1 | * | 2/2001 | Ogle et al. | 250/227.14 |
| 6,289,741 B1 | * | 9/2001 | Ghetzler et al. | 73/150 A |

OTHER PUBLICATIONS

James M. Gere; Stephen P. Timoshenko; (1878–1972), PWS Publishing Co., Fourth Edition, Mechanics of Materials, pp. 2 through 4.

Daniel Frederick; Tien Sun Chang; Scientific Publishers, Inc., Boston, 1972; Continuum Mechanics; pp. 5–9.

* cited by examiner

*Primary Examiner*—Max Noori  
(74) *Attorney, Agent, or Firm*—Whitham, Curtis & Christofferson, P.C.

(57) ABSTRACT

A method and apparatus for determining bulk material constants such as Poisson's ratio and the ratio of shear modulus to bulk modulus for elastomeric materials, including, but not limited to elastomers, rubbers, gels and sealants is disclosed. The bulk material properties are determined by measuring the pressure change of the elastomeric material when the elastomeric material is subjected to an applied pressure. The changes in the bulk material property due to temperature or a the addition of a diluent may also be determined. The apparatus includes a container that holds the elastomeric material. A pressure sensor is located in the container and is positioned to measure the pressure of the elastomeric material. The signal from the pressure sensor along with the applied pressure is used to determine a bulk material property such as Poisson's ratio or the ratio of shear modulus to bulk modulus for the elastomeric material.

22 Claims, 8 Drawing Sheets

METHOD AND APPARATUS FOR DETERMINING BULK MATERIAL PROPERTIES OF ELASTOMERIC MATERIALS

The present application is based on U.S. Provisional Application No. 60/194,400 filed on Apr. 4, 2000, herein incorporated by reference in its entirety.

FIELD OF THE INVENTION

The present invention is directed to a method and apparatus for determining bulk material properties of elastomeric materials. Further, the present invention is directed to a method and apparatus for measuring the change in pressure in an elastomeric material due to an applied force for determining the ratio of shear modulus to bulk modulus and Poisson's ratio for the elastomeric material.

BACKGROUND OF THE INVENTION

Elastomers and gel-like polymers are widely used as sealants, damping materials, or structural elements, and the like. Bulk material properties such as the bulk modulus, the shear modulus, and Poisson's ratio are important properties in polymer engineering. Once these properties are determined, the mechanical properties of the elastomeric material may be determined. The mechanical design and application of an elastomeric material will often depend on its bulk material properties.

The experimental determination of elastomeric material properties is known to be a delicate and difficult task. Some procedures for measuring material properties involve measuring the change in volume of the elastomeric material. These measurements are often needed to four or more significant digits. This accuracy typically requires expensive instrumentation, such as a highly sensitive extensometer or precise optical measurement apparatus, to measure the slight volume change. These experimental procedures are prone to error due to the very small volume change in the elastomeric materials. Further, voids which are inevitable in polymers greatly influence any measured volume change.

There is a need for a method and apparatus that provides improved accuracy and reproducibility for measuring the bulk material properties of an elastomeric material.

SUMMARY OF THE INVENTION

Accordingly, the present invention is directed to a method for measuring bulk material properties of an elastomeric material. The method includes applying pressure to an elastomeric material in a container, measuring the pressure of the elastomeric material from a signal generated by a pressure sensor in the container, and determining a bulk material property for the elastomeric material using the signal from the pressure sensor and the magnitude of the applied pressure. The bulk material property may include Poisson's ratio and the ratio of shear modulus to bulk modulus.

The method may include determining the coefficient of thermal expansion for the elastomeric material from the determined bulk material property. Further, the method may include the steps of adding a diluent to the elastomeric material, and determining the coefficient of diluent expansion for the elastomeric material from the change in bulk material property as a function of diluent addition.

The method of the present invention may also include the step of comparing the determined bulk material property of the elastomeric material with a known or desired bulk material property.

The present invention also includes an apparatus for determining a bulk material property of an elastomeric material. The apparatus includes a container having a cavity adapted to hold an elastomeric material and a means for applying pressure to an elastomeric material contained in the cavity. The apparatus also includes a pressure sensor in the cavity adapted to measure the pressure of the elastomeric material, and a means for determining a bulk material property of the elastomeric material in communication with the pressure sensor. The means for determining a bulk material property of the elastomeric material uses the measured pressure from the pressure sensor and the applied pressure to determine the bulk material property. The bulk material property may include Poisson's ratio and the ratio of shear modulus to bulk modulus. The container may be made of steel, aluminum or the like. The cavities are preferably cylindrical and have a height greater than the radius of the cavity.

The apparatus may include an applied pressure sensor in the cavity adapted to measure the applied pressure. Further an environmental chamber surrounding the container wherein the environmental chamber controls the temperature of the container may also be included in the apparatus.

Still further, the apparatus may include a diluent addition source in communication with the cavity of the container that is adapted to add a diluent to the elastomeric material. The diluent may include air, gas, hydrocarbon gases, organic gases, liquids, hydrocarbon liquids, organic liquids, or combinations thereof.

The apparatus may include a means for determining the coefficient of thermal expansion for the elastomeric material from a change in the bulk material property as a function of temperature. The means for determining the coefficient of thermal expansion may be an electronic device.

The means for applying pressure to the elastomeric material may include a pressure chamber above the cavity. Further, the means for applying pressure to the elastomeric material may be a piston adapted to be slidably received in the cavity of the container.

The means for determining a bulk material property of the elastomeric material may include an electronic device such as a computer or handheld device.

The apparatus may also include a plurality of cavities in the container and a pressure sensor for each of the plurality of cavities. The geometric configuration for each cavity may be the same or different from one another.

The present invention also includes an impact force sensor. The force sensor includes a sealed container having an elastomeric material with known bulk material properties contained therein and an air chamber in the sealed container located above the elastomeric material. The force sensor also includes a first pressure sensor in the air chamber adapted to measure the pressure in the air chamber and a second pressure sensor in the container adapted to measure the pressure of the elastomeric material. A means for determining an impact force when the sensor is subjected to an impact is positioned in communication with the first and second pressure sensors. The means for determining an impact force uses the measured pressures between the first and second pressure sensors and the known bulk material constant of the elastomeric material to determine the impact force. The means for determining an impact force may include an electronic device.

Still further, the present invention includes an apparatus for determining a bulk material property of a polymer with temperature compensation. The apparatus includes a first container having a cavity adapted to hold an elastomeric material and a means for applying pressure to an elastomeric material contained in the first cavity. Also included is a first pressure sensor in the first cavity adapted to measure the pressure of the elastomeric material and a second container having a cavity adapted to hold the elastomeric material. A second pressure sensor is located in the second cavity and is adapted to measure the pressure of the elastomeric material. A means for determining a bulk material property of the elastomeric material is in communication with the first and second pressure sensors and uses the measured pressures from the first and second pressure sensors and the applied pressure to determine the bulk material property of the elastomeric material. The bulk material property may include Poisson's ratio or the ratio of shear modulus to bulk modulus.

DETAILED DESCRIPTION OF THE INVENTION

The Poisson's ratio v of elastomeric materials is a somewhat ambiguous and misunderstood material constant. Poisson's ratios for elastomeric materials are very close to 0.5, which is the ratio of a true incompressible material, but are always less than 0.5 because of their slight compressibility. Such deviations are small but play a significant role in determining how the material will respond, especially in force transmission when the materials are constrained. For example, the isotropic bulk modulus K is related to the Young's modulus E via $$K = \frac{E}{3(1-2v)},$$

and as one can see, K is very sensitive to v when near 0.5. Therefore, depending on the elastomeric material, Poisson's ratio v may be needed with accuracy of up to five significant digits, if not more, to determine the bulk material property. This accuracy often requires expensive instrumentation, such as a highly sensitive extensometer or precise optical measurement apparatus to measure the slight volume changes.

As used herein, "elastomeric materials" are polymers having chemical or physical cross-links and include, but are not limited to elastomers, rubbers, gels, and soft compressible polymeric materials.

Assuming elastomeric materials to be purely elastic and isotropic materials, the present invention is directed to a technique for measuring Poisson's ratio without directly measuring the volume change. Rather, the force transmission is measured for a constrained elastomeric cylinder to characterize the Poisson's ratio, based on a closed-form solution that has its foundations in the Volkersen shear lag concept. Once Poisson's ratio is determined, the bulk modulus K can be derived from the elastic constant E or shear modulus G, which can be easily measured experimentally through dynamic mechanical analysis. The shear modulus G is related to the elastic constant E by G=E/2(1+v). Once these bulk material properties are determined for an elastomeric material, one will be able to use these values to determine whether a particular elastomeric material will be appropriate for a particular use or application.

The theoretical analysis of the experimental technique and the details of the apparatus for measuring the bulk material properties of elastomeric material are discussed below. Further, a system for measuring the bulk material properties of elastomeric materials under high pressure is also discussed.

Figure 1:
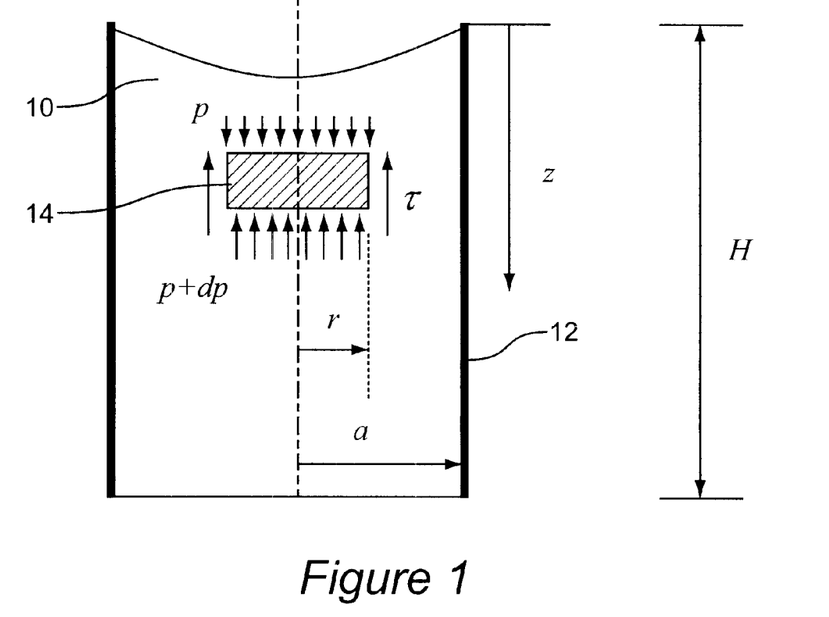
FIG. 1 is a diagram illustrating the force balance of a circular disk element of the elastomeric material.

With reference now to FIG. 1, we consider an elastomeric material 10 constrained in a rigid cylindrical wall 12 of radius a and depth H. The top surface sustains a uniform pressure $p_0$ and the bottom surface is completely sealed (i.e., a rigid wall). The elastomeric material is assumed to be elastic and isotropic, and its bulk modulus K is much higher than the shear modulus G. We further assume that the elastomeric material is bonded to the cylinder wall permitting no relative movement, and the length of the cylinder is large compared to the radius of the cylinder so that the pressure p may be considered to be a function of the depth, or the axial direction, z, but independent of radius, i.e., p=p(z).

With continuing reference to FIG. 1, consider a circular disk element 14 of the elastomeric material 10. In order to satisfy the force balance, we see that $$\frac{dp(z)}{dz} = -\frac{2}{r}\tau \qquad (1)$$

If u(r,z) is the deformation field, it relates to the shear stress τ via $$\tau = G\frac{\partial u}{\partial r}. \qquad (2)$$

From equations (1) and (2) and the condition that u(a,z)=0 since the material is bonded to the cylinder wall, we find that the deformation field u(r,z) is parabolic:

$$u(r, z) = q(z)\left(1 - \frac{r^2}{a^2}\right), \qquad (3)$$

where q(z) is the (maximum) deflection of the elastomeric material at the center, and is of the form $$q(z) = \frac{a^2}{4G} \frac{dp(z)}{dz}. \qquad (4)$$

The volume change can be further expressed in the form by integrating the displacement field $$\Delta V(z) = \frac{\pi a^2 [q(z) - q(H)]}{2}, \qquad (5)$$

where $q(H)$ is the axial deformation at the bottom of the elastomeric material. If the stress state is assumed to be hydrostatic for $V\sim0.5$, we may write the relation $$q(z) - q(H) = 2 \int_0^z \frac{p(\bar{z})d\bar{z}}{K}. \qquad (6)$$

Invoking equations (4) and (6), we arrive at the differential equation for the pressure function $$\frac{d^2 p(z)}{dz^2} - \lambda^2 p(z) = 0. \qquad (7)$$

The solution of (7) is in the form of hyperbolic sine and cosine function where $$p(z) = A\sinh\left(\bar{\lambda}\left(\frac{z}{H} - 1\right)\right) + B\cosh\left(\bar{\lambda}\left(\frac{z}{H} - 1\right)\right). \qquad (8)$$

and the non-dimensional parameter is $$\bar{\lambda} = \lambda H = \sqrt{\frac{8G}{K}} \frac{H}{a} = \sqrt{\frac{12(1-2v)}{1+v}} \frac{H}{a}. \qquad (9)$$

A and B are integration constants determined by the boundary conditions. To measure the bulk material properties in a sealed end apparatus, the boundary conditions are $$p = p_0 \text{ at } z = 0$$

and $$\frac{dp}{dz} = 0$$

at $z=H$, and the solution becomes $$\frac{p(z)}{p_0} = \frac{\cosh\left(\bar{\lambda}\left(\frac{z}{H} - 1\right)\right)}{\cosh(\bar{\lambda})}. \qquad (10)$$

If the sensor is mounted at the bottom of the cylindrical tube, $z/H=1$ and gives the following relationship $$\frac{p_b}{p_0} = \left(\cosh\left(\frac{H}{a}\sqrt{\frac{12(1-2v)}{(1+v)}}\right)\right)^{-1}. \qquad (11)$$

To include the temperature effect, we must include the volume expansion due to the coefficient of thermal expansion (CTE), $\alpha$. The differential equation (7) is now of the form $$\frac{d^2 p(z)}{dz^2} - \lambda^2 p(z) = \alpha \lambda^2 K(\theta - \theta_0). \qquad (12)$$

Now, the solution of the equation becomes $$p(z) = A'\sinh\left(\bar{\lambda}\left(\frac{z}{H} - 1\right)\right) + B'\cosh\left(\bar{\lambda}\left(\frac{z}{H} - 1\right)\right) + \alpha KT, \qquad (13)$$

where $T=\theta-\theta_0$ is the difference between the applied temperature and the stress-free temperature when the thermal-induced pressure $p(z)$ is null. Solving the integration constants A' and B' for a gel of close end boundary condition, we see the bottom pressure is expressed by $$p_b = (p_0 - \alpha KT)\left(\cosh\left(\frac{H}{a}\sqrt{\frac{12(1-2v)}{(1+v)}}\right)\right)^{-1} + \alpha KT. \qquad (14)$$

If the temperature is fixed and we have two applied pressures $p_{01}$ and $p_{02}$ with output pressures $p_{b1}$ and $p_{b2}$, respectively, we have, after simplification, $$\frac{p_{b1} - p_{b2}}{p_{01} - p_{02}} = \left(\cosh\left(\frac{H}{a}\sqrt{\frac{12(1-2v)}{(1+v)}}\right)\right)^{-1}. \qquad (15)$$

Note that in (3), the term $\alpha KT$ cancels out. The slope of $p_b$ vs. $p_0$ would determine Poisson's ratio $v$. This equation is similar to one when the temperature effect is neglected, but here in (15), the terms are the differences of output pressures and applied pressures.

Figure 2:
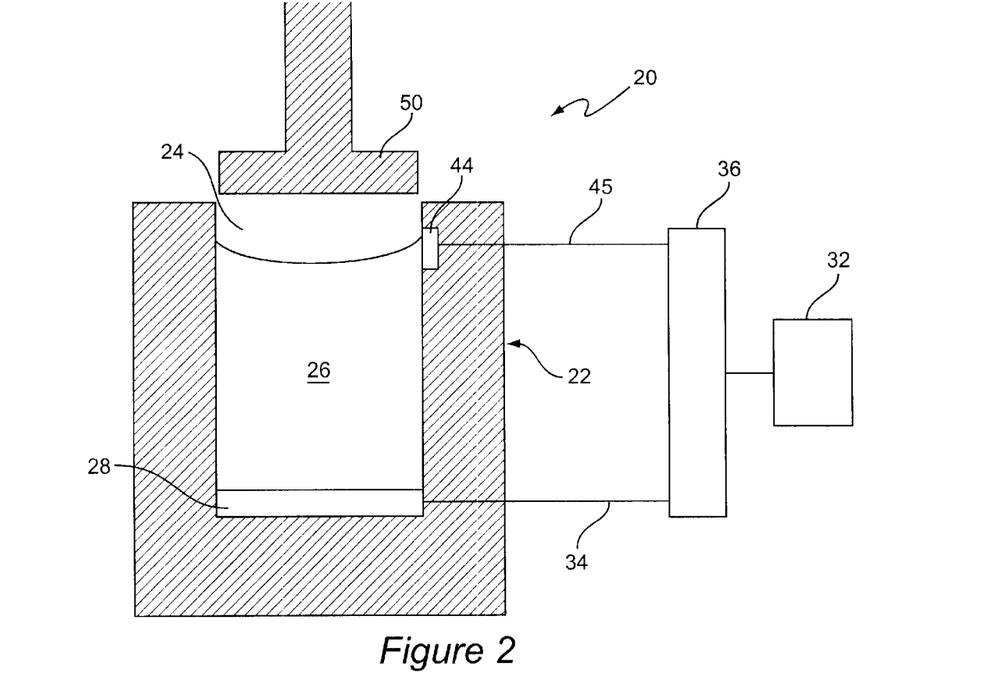
FIG. 2 is a cross-sectional view of an apparatus in accordance with one embodiment of the present invention.

With reference now to FIG. 2 there is shown an apparatus 20 for determining the bulk material properties of an elastomeric material. Generally, The apparatus includes a container 22 having a cavity 24 for receiving an elastomeric material 26. The container 22 should be made of a material that is relatively inflexible when the elastomeric material is under pressure. Preferably, the container is a made from a material that has an elastic constant or Young's modulus that is about two orders of magnitude greater than elastic constant or Young's modulus of the elastomeric material. Materials for the container 22 may include, but are not limited to, aluminum, steel, stainless steel, alloys of steel, and the like. Other metals and plastic materials may be suitable depending on the pressure that will be applied and elastomeric material being tested.

Figure 3:
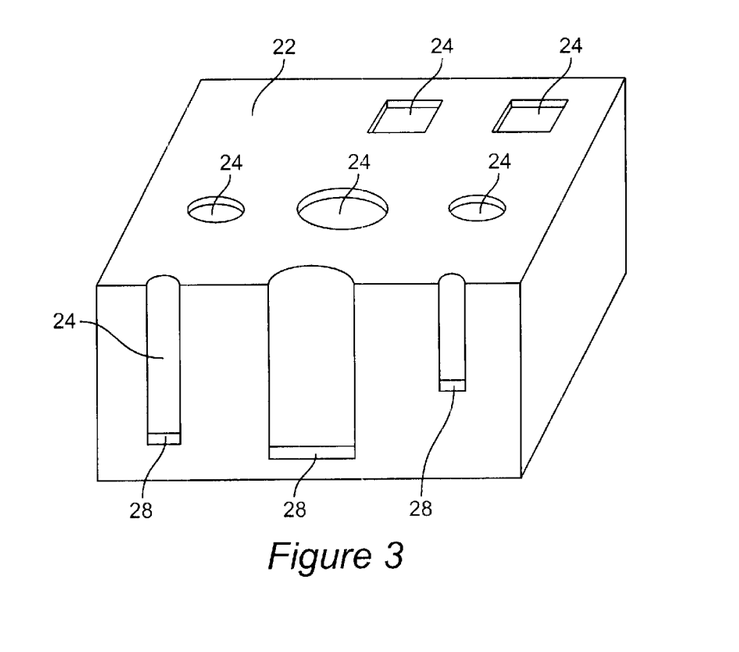
FIG. 3 is a cross-sectional view of a container in accordance with one embodiment of the present invention.

As shown in FIG. 3, the container 22 may have one or more cavities 24 contained therein. Further, the geometric configuration, such as the height, radius, and shape, of the cavity may vary. In a preferred embodiment, the height of the cavity is greater than the radius of the cavity. Most preferably, the cavity is cylindrically shaped and has a height to radius ratio ranging from about 15 to about 20. The cavity may take on other shapes. Elliptical, square, rectangle, or polygonal cross-sectional shapes for the cavity may be used.

As shown in FIG. 3, the container 22 may contain a plurality of cavities 24. In this configuration, the cavities may have the same or different geometric configuration. FIG. 3 illustrates cavities that have varying radii. Alternatively, various combinations of cavities 24 having different radial dimensions, height and cross-sectional shapes may be included in one container 22. For example, a stainless steel or aluminum block may have a plurality of cavities bored into one side of the block.

Figure 4:
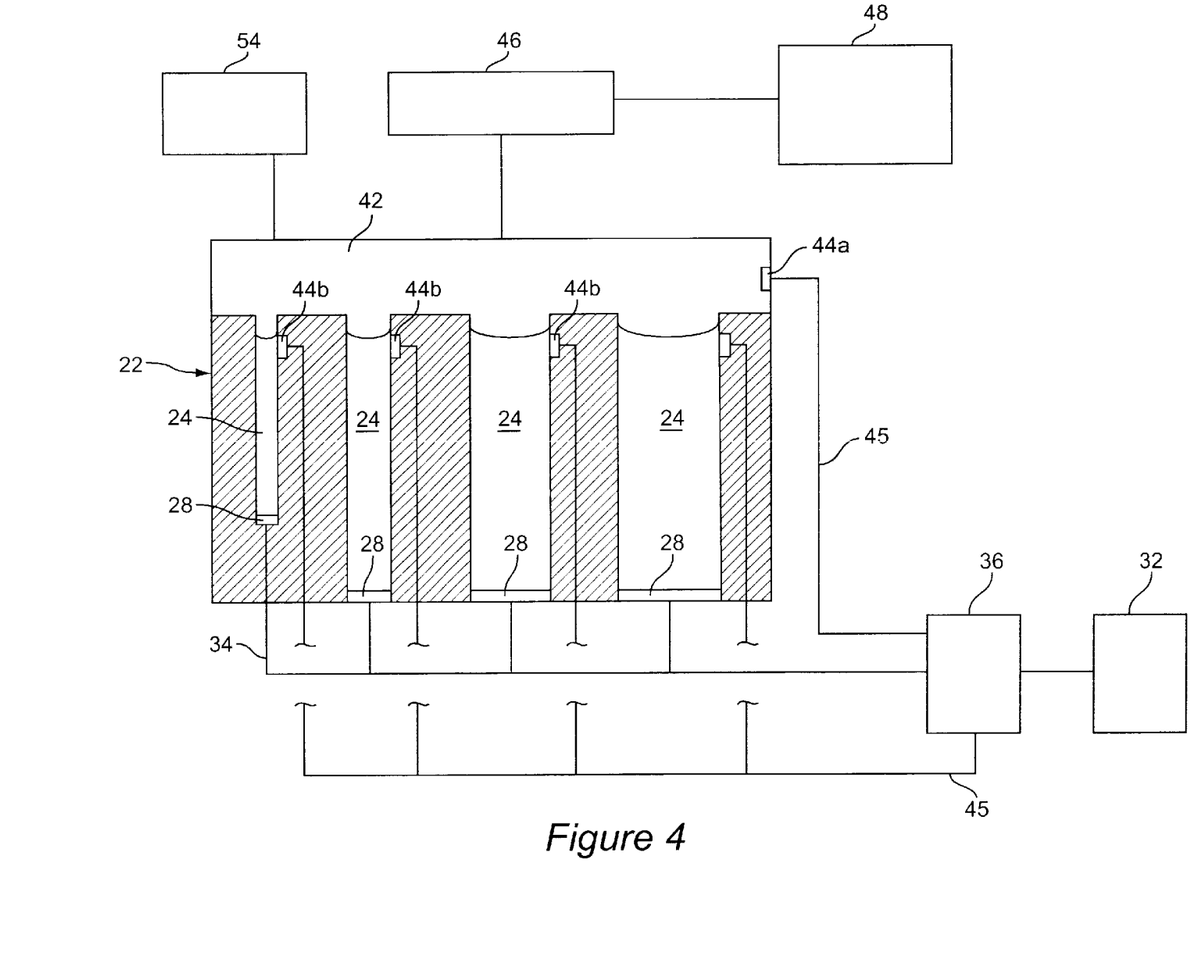
FIG. 4 a cross-sectional view of an apparatus in accordance with another embodiment of the present invention.

With reference now to FIGS. 2–4, a pressure sensor 28 is used to measure the pressure of the elastomeric material when a pressure is applied to the elastomeric material. The pressure sensor 28 should be located in the container such that the pressure sensor 28 will be able to measure the pressure of the elastomeric material resulting from the applied pressure. Preferably, the pressure sensor 28 is located in the container near the bottom of the cavity. Most preferably, the pressure sensor 28 is located at the bottom of the cavity.

The type of pressure sensor 28 is not critical. The pressure sensor 28 preferably generates a pressure related signal that is accurate to four or more significant figures. Suitable types of pressure sensors may include, but are not limited to, steel diaphragm type pressure transducers, piezo type pressure transducers, silicon-based micro electro-mechanical pressure transducers, or other similar pressure transducers.

The signal from the pressure sensor 28 is preferably routed to an electronic device 32 for analysis of the bulk material properties through signal leads 34 from the pressure sensor 28. The electronic device 32 may be a hand held unit or a computer. The electronic device 32 needs to be programmable to the extent that signals generated from the pressure sensors are applied to the above equations to determine the bulk material properties, such as Poisson's ratio, of the elastomeric material.

The signal from the pressure sensor 28 may be routed to the electronic device 32 through a general purpose interface board 36 which may include an analog to digital converter. If the signals from the pressure sensors 28 are analog signals, the signals should go through an analog to digital converter prior to going to the electronic device 32. Alternatively, the electronic device may be equipped with an appropriate interface or analog to digital converter such that the signal from the pressure sensor is routed directly to the electronic device 32. If the pressure sensor 28 generates a digital signal, the analog to digital converter may not be necessary. The pressure sensor 28 may be provided with a direct pressure readout display 38 for manual monitoring the pressure of the elastomeric material.

With reference now to FIGS. 2–5, a means for applying pressure 40 to the elastomeric material is located near the top of the container 22. Preferably, the means for applying pressure is above the container 22 and opposite the pressure sensor 28. The means for applying pressure 40 may be any pressure applicator that is capable of exerting a controlled pressure to the elastomeric material. In one embodiment, illustrated in FIG. 4, compressed air or other gas or liquid from a source 48 may be used to fill a pressure chamber 42 that is above the elastomeric material. Filling the pressure chamber with a liquid or gas to a certain pressure will result in an applied pressure to the elastomeric material in the container 22. An alternative embodiment is illustrated in FIG. 2 and uses a piston 50 or other similar mechanical device to apply pressure to the elastomeric material.

In order to determine the bulk material properties in accordance with the present invention, the applied pressure to the elastomeric material must be known. Accordingly, an applied pressure sensor 44 may be used for monitoring the applied pressure. The applied pressure sensor may be located in the pressure chamber 42a shown by reference numeral 44a or near the top of the cavity 24 in the container 22 as shown by the reference numeral 44b. Where compressed air or liquid is used to apply pressure to the elastomeric material, a regulator 46 between pressure chamber 42 and the compressed air or liquid source 48, if accurate enough, may be used to determine the applied pressure to the elastomeric materials. The applied pressure sensor 44 preferably generates a pressure related signal that is accurate to four significant figures. When an applied pressure sensor is used, the signal is preferably routed to the electronic device 32 through leads 45.

Where a piston 50 or the like is used to apply the pressure, the applied pressure sensor 44 is preferably located near the top of the cavity 24 in the container 22. Alternatively, the piston 50 may have a controller that provides the applied pressure information that can then be used to determine the bulk material properties of the elastomeric material in accordance with the present invention.

Figure 5:
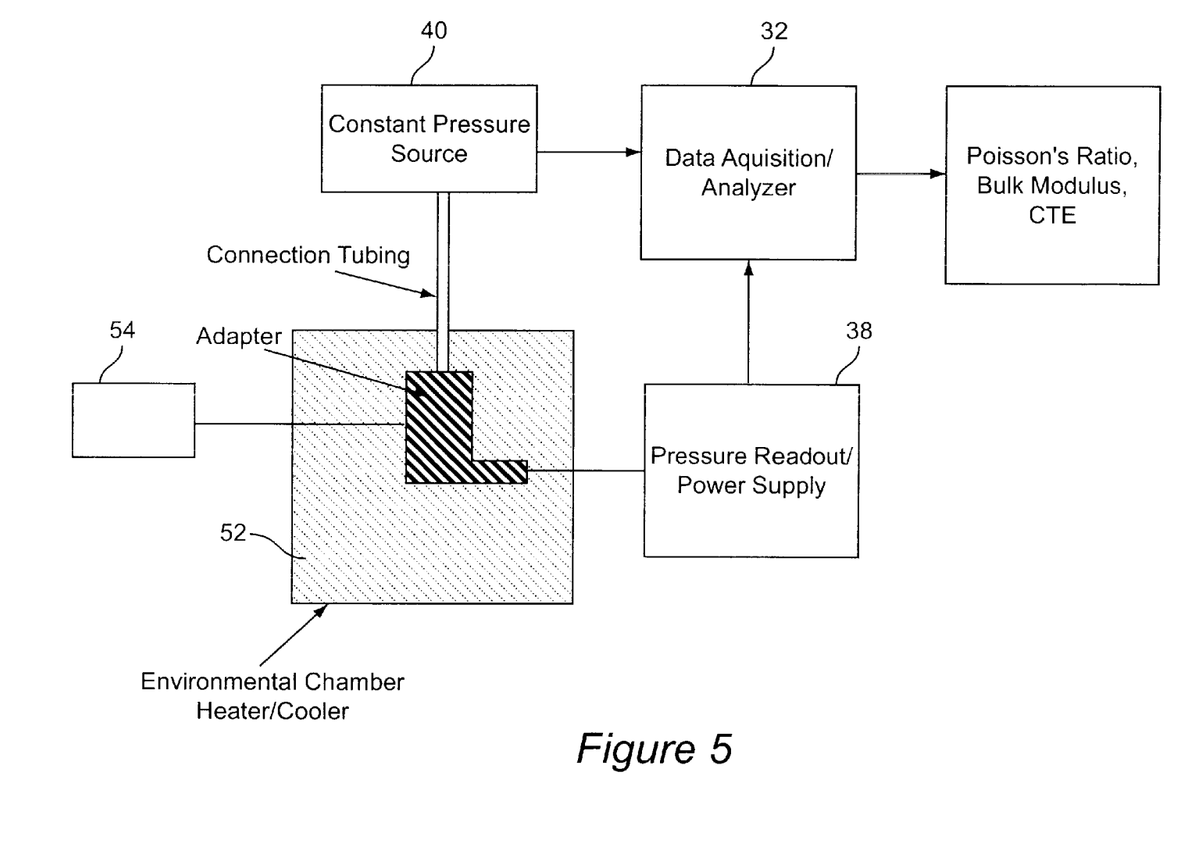
FIG. 5 a diagrammatic view of an apparatus with an environmental chamber in accordance with yet another embodiment of the present invention.

As illustrated in FIG. 5, the container 22 may be placed in an environmental chamber 52 to control the conditions under which the elastomeric material is experiencing the applied pressure. The environmental chamber 52 may consist of a temperature control device such as a heater or refrigeration device to control the temperature of the elastomeric material and create a temperature field surrounding the elastomeric material. Further, diluent addition sources 54 for adding various diluents to the elastomeric material may be included. Diluents may include but are not limited to water, liquid hydrocarbons, other liquid organics, air, gas, hydrocarbon gases, organic gases, or combination thereof. By adding diluents to the elastomeric material, the change in the bulk material properties of the elastomeric material due to the added diluent may be determined.

Now that the basic device of the present invention has been described, the method for determining the bulk materials of the elastomeric material will be described. First the elastomeric material 26 to be studied is loaded in the cavity 24 of the container 22. Pressure is then applied to the elastomeric material. The signal from the pressure sensor 28 and the applied pressure information is collected. This information is then used to calculate bulk material properties of the elastomeric material such as Poisson's ratio and the ratio of shear modulus to bulk modulus using the above described equations. A preferred equation is equation (15). The ratio of shear modulus G to bulk modulus K may also be determined and is related to Poisson's ratio v by $G/K = (3(1-2v))/(2(1+v))$.

The method can be repeated under different applied pressures and conditions to determine the effect of temperature or diluents on the bulk material properties of the elastomeric material. Additionally, having determined the bulk material properties of the elastomeric material, one skilled in the art would be able to determine material constants such as the coefficient of thermal expansion, and the coefficient of diluent expansion using the previously described relationships.

The device may be used to determine how the bulk material properties of one elastomeric material differs from an elastomeric material with known bulk material properties. Accordingly, one will be able to determine whether the tested elastomeric material meets specified bulk material properties. Such a method and device can be used for quality control in making elastomeric materials to ensure that the elastomeric materials meets specifications. Further, the method may be used for monitoring the progress of the reaction for forming the elastomeric material.

Figure 6:
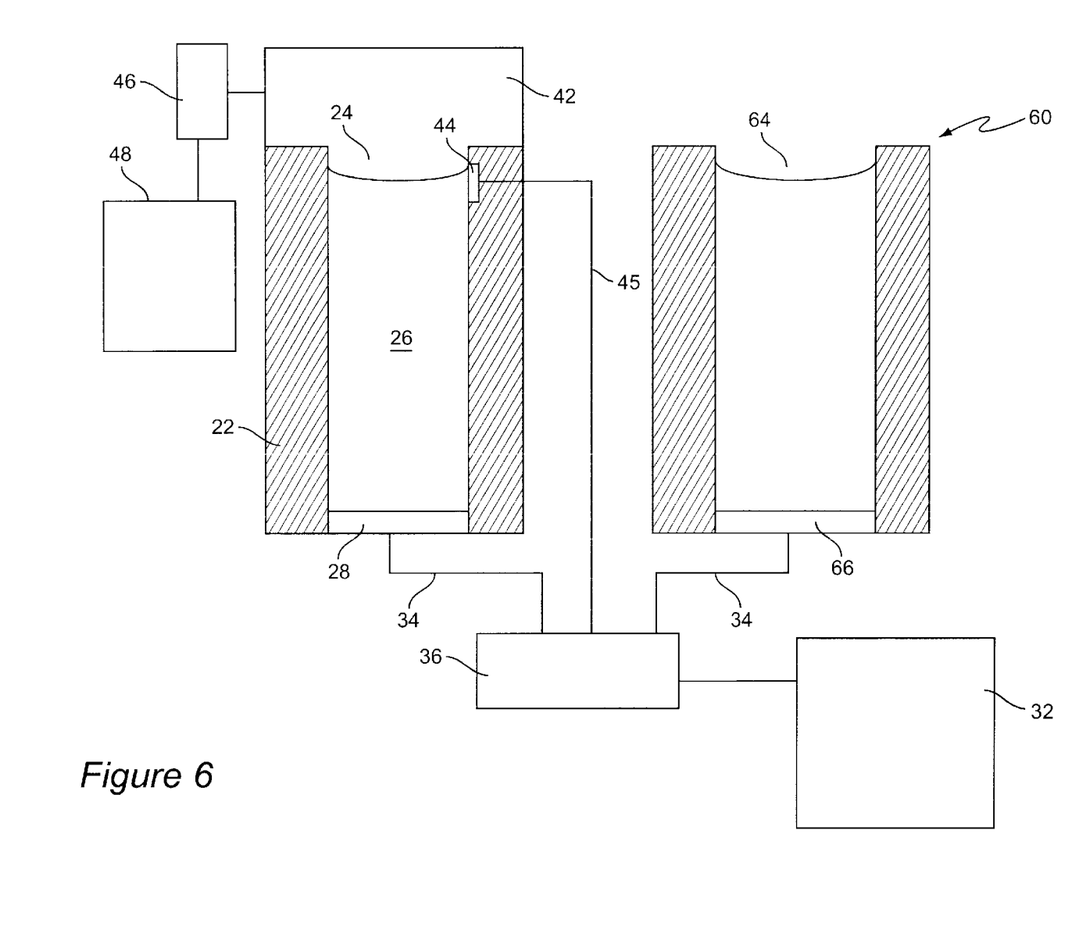
FIG. 6 a cross-sectional view of an apparatus with temperature compensation in accordance with still another embodiment of the present invention.

With reference now to FIG. 6, another embodiment of the present invention includes the same basic apparatus for measuring the bulk properties of an elastomeric material but also includes a second device 60 for measuring the pressure of the elastomeric material without an applied pressure. FIG. 6 shows the basic apparatus have a container 22, a cavity 24, an elastomeric material 26 in the cavity, a pressure sensor 28 near the bottom of the cavity, and an applied pressure sensor 44 near the top of the cavity. The basic apparatus is shown with a pressure chamber 42 located above the cavity 24. Alternatively, a piston may be used to apply pressure to the elastomer.

The second device 60 is configured similarly to the basic apparatus except that the second device does not need a sensor for monitoring the applied pressure. The second device includes a container 62 with a cavity 64. A second pressure sensor 66 is preferably located near the bottom of the cavity. The signals from the pressure sensors 28 and 66 are collected by and electronic device 32 as described above.

By providing the second device 60 that does not experience the applied pressure, the pressure signal from the second device may be subtracted from the pressure signal from the basic apparatus. In this way, the second device acts as a temperature compensation device by subtracting out the contribution to the pressure reading due to temperature.

Figure 7:
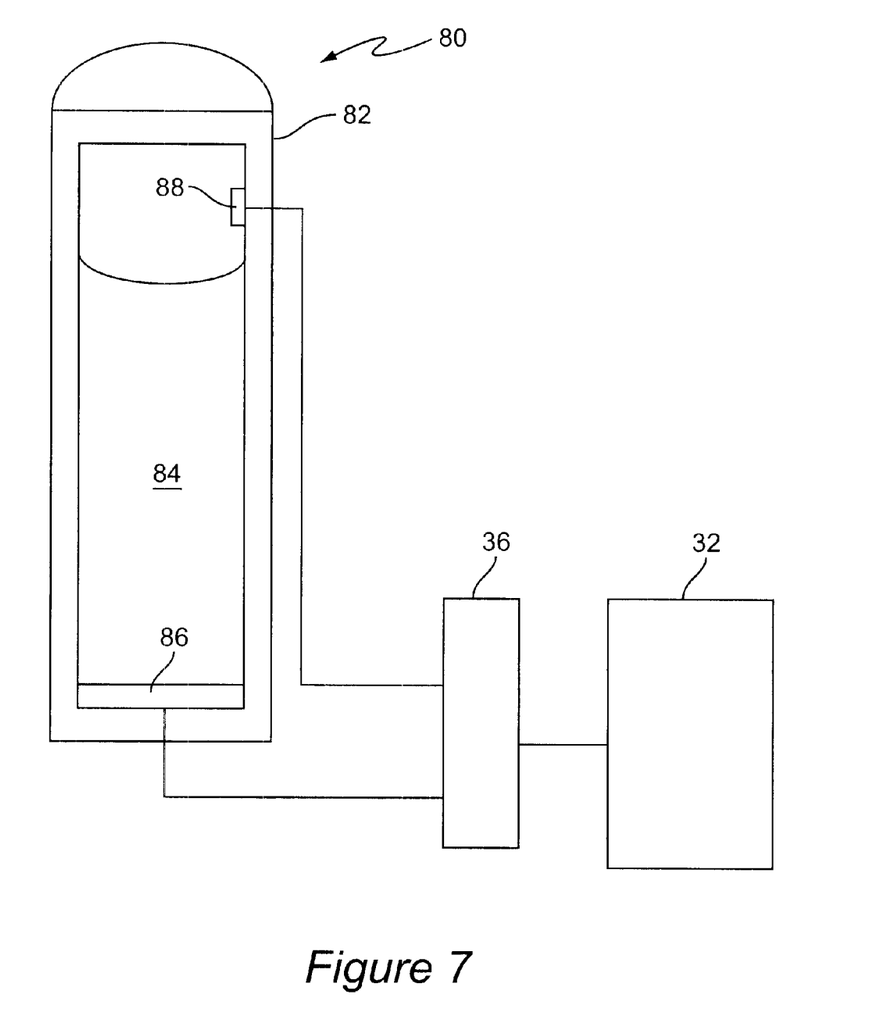
FIG. 7 a cross-sectional view of a force sensor in accordance with an embodiment of the present invention.

Another embodiment of the present invention is illustrated in FIG. 7 and is directed to an impact or inertial force sensor 80. The force sensor 80 includes a container 82 filled with an elastomeric material 84 that has known bulk material properties. A pressure sensor 86 is located near the bottom of the container and measures the pressure of the elastomeric material. The container is closed at the top and bottom. Preferably, there is a gap between the top of the elastomeric material 84 and the top of the container 82. The gap may be filled with compressed air. An initial pressure sensor 88 is located in the gap for measuring the initial pressure. Both the pressure sensor 86 and the initial pressure sensor 88 are connected to an electrical device as described above. The force sensor may be used to determine the impact force from and impact source.

When the force sensor experiences an impact, the force is transmitted from the top of the container 82, through the gap and the elastomeric material 84. The pressure sensor 86 and the initial pressure sensor 88 will measure the pressure experienced at the top and bottom of the elastomeric materials. Because the bulk material properties of the elastomeric material and the pressures from the impact are known, the above described relationships can be used to determine the original impact force applied to the force sensor. This type of force sensor may be particularly useful in accelerometers or other devices where the force of an impact needs to be measured. The shape of the force sensor may vary. The force sensor is preferably cylindrical.

The present invention is illustrated in the following examples. The example is provided for illustration purposes and should not be construed as limiting the scope of the present invention.

EXAMPLES

Two different gels were tested in the basic apparatus illustrated in FIG. 2. Before each gel was tested, they were treated in the following manner. The gel is put into a vacuum chamber for about 5 minutes, allowing the bubbles within the gel to escape. The gel is then poured into the container with the gel weight carefully measured, so the aspect ratio of the gel in the cylinder can be calculated. The container and gel is placed under vacuum for about 5 minutes to remove any bubbles due to the pouring of the gel to the cylinder. The gel was then cured in the container. For the gel 2, the curing scheme was one hour under 150 ° C.

Figure 8:
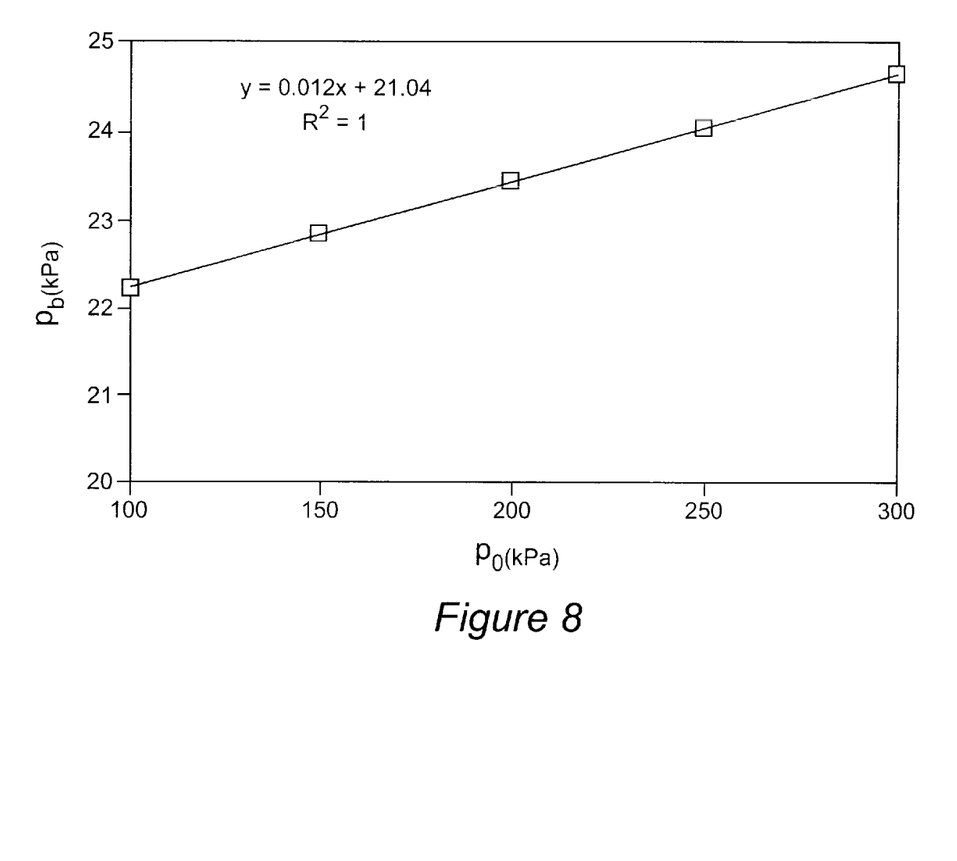
FIG. 8 is a plot of applied pressure vs. the bottom pressure for gel 1.

Gel 1: FIG. 8 shows the plot of applied pressure vs. the bottom pressure. The applied pressure p0 was ramped up and down, and the corresponding bottom pressure pb was measured. No hysteresis was found in the experimental results. A total of 5 cc of gel was poured into the cylinder resulting an aspect ratio H/a=13.65. Based on the slope of this plot and equation (15), we readily find that the Poisson's ratio of the gel is v=0.49127. The Young's modulus of the gel is 230 KPa, so the bulk modulus K=4.39 MPa.

The value is much lower than the expected bulk modulus of gel, which is normally in the range of 1 GPa. Micro voids within the gel may have played a role in reducing the bulk modulus. Because there was no hysteresis observed in the pressure plot, we do not think there was any debond between the gel and the cylinder wall.

Figure 9:
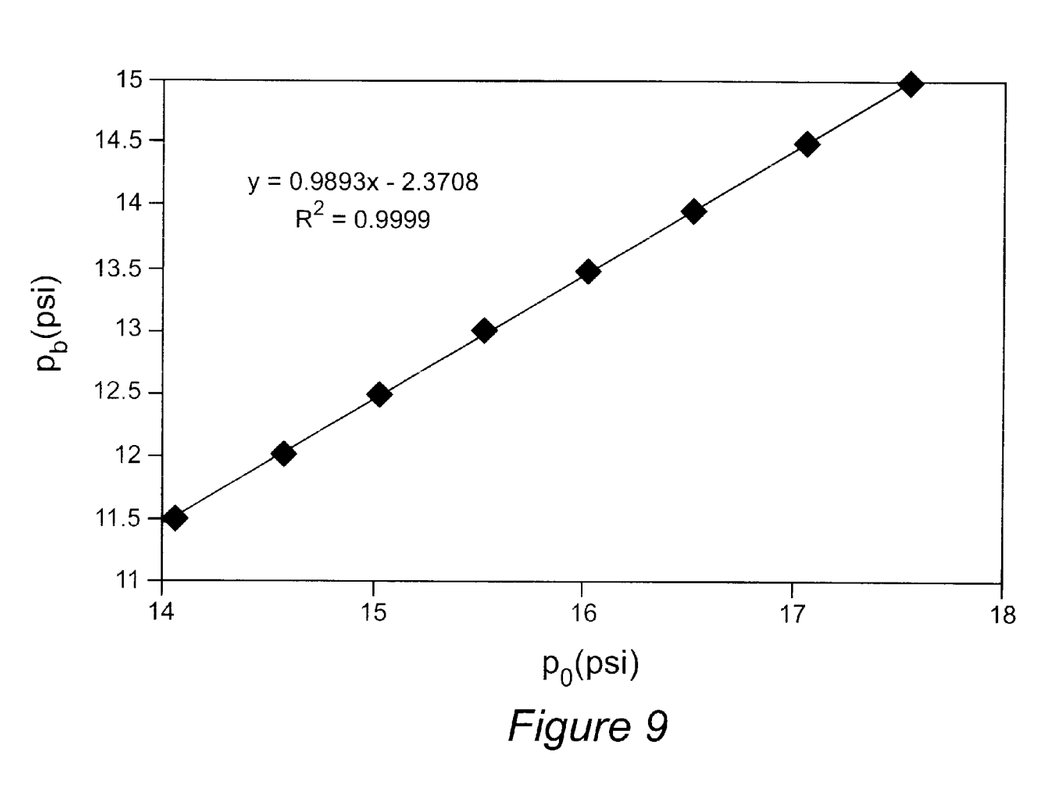
FIG. 9 is a plot of applied pressure vs. the bottom pressure for gel 2.

Gel 2: The second gel was a harder gel with an elastic modulus E=60 KPa. FIG. 9 is a plot of the applied pressure vs. the bottom pressure. We calculated the bottom pressure based on the calibration chart that we generated. A total of 8.1353 g of gel (or 4.4712 c.c.) was poured into the cylinder resulting an aspect ratio H/a=12.206. Based on the slope of this plot 0.9893 and (15), we readily find that the Poisson's ratio of the gel is v=0.499992, and the bulk modulus K=1.25 GPa. This result appears to be of the value which we would expect for polymeric gels, i.e., the bulk modulus is in the range of 1 GPa.

It will be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description without departing from the substance or scope of the present invention.

What is claimed is:

1. A method for measuring bulk material properties of an elastomeric material comprising the steps of:

applying pressure to an elastomeric material in a container which prevents radial expansion of said elastomeric material;

measuring the pressure of the elastomeric material from a signal generated by a pressure sensor in the container; and determining a bulk material property selected from the group consisting of Poisson's ratio and a ratio of shear modulus to bulk modulus for the elastomeric material using (A) the signal from the pressure sensor and (B) the magnitude of the applied pressure.

2. The method of claim 1 further comprising the steps of:

applying a temperature field to the elastomeric material; and determining the coefficient of thermal expansion for the elastomeric material from the change in the bulk material property as a function of temperature.

3. A method for measuring bulk material properties of an elastomeric material comprising the steps of:

applying pressure to an elastomeric material in a container;

measuring the pressure of the elastomeric material from a signal generated by a pressure sensor in the container;

determining a bulk material property for the elastomeric material using the signal from the pressure sensor and the magnitude of the applied pressure;

adding a diluent to the elastomeric material; and determining the coefficient of diluent expansion for the elastomeric material from the change in the bulk material property as a function of diluent addition.

4. The method of claim 1 further comprising the step of comparing the determined bulk material property of the elastomeric material with a known bulk material property.

5. An apparatus for determining a bulk material property of an elastomeric material comprising:
   a container having a cavity adapted to hold an elastomeric material and which prevents radial expansion of said elastomeric material;
   means for applying pressure to an elastomeric material contained in the cavity;
   a pressure sensor in the cavity adapted to measure the pressure of the elastomeric material; and
   means for determining a bulk material property of the elastomeric material (wherein the bulk material property is selected from the group consisting of Poisson's ratio and a ratio of shear modulus to bulk modulus) in communication with the pressure sensor wherein the means for determining a bulk material property of the elastomeric material uses (A) the measured pressure from the pressure sensor and (B) the applied pressure to determine the bulk material property.

6. The apparatus of claim 5 further comprising an applied pressure sensor in the cavity adapted to measure the applied pressure.

7. The apparatus of claim 5 further comprising an environmental chamber surrounding the container wherein the environmental chamber controls the temperature of the container.

8. An apparatus for determining a bulk material property of an elastomeric material comprising:
   a container having a cavity adapted to hold an elastomeric material;
   means for applying pressure to an elastomeric material contained in the cavity;
   a pressure sensor in the cavity adapted to measure the pressure of the elastomeric material;
   means for determining a bulk material property of the elastomeric material in communication with the pressure sensor wherein the means for determining a bulk material property of the elastomeric material uses the measured pressure from the pressure sensor and the applied pressure to determine the bulk material property; and
   a diluent addition source in communication with the cavity of the container and adapted to add a diluent to the elastomeric material.

9. The apparatus of claim 8 wherein the diluent is selected from the group consisting of air, gas, hydrocarbon gases, organic gases, liquids, hydrocarbon liquids, organic liquids, or combinations thereof.

10. The apparatus of claim 8 further comprising a means for determining the coefficient of thermal expansion for the elastomeric material from a change in the bulk material property as a function of temperature.

11. The apparatus of claim 10 wherein the means for determining the coefficient of thermal expansion is an electronic device.

12. The apparatus of claim 5 wherein the means for applying pressure to the elastomeric material is a pressure chamber above the cavity.

13. The apparatus of claim 5 wherein the means for applying pressure to the elastomeric material is a piston adapted to be slidably received in the cavity of the container.

14. The apparatus of claim 5 wherein the means for determining a bulk material property of the elastomeric material is an electronic device.

15. The apparatus of claim 5 further comprising a means for determining the coefficient of thermal expansion for the elastomeric material from a change in the bulk material property as a function of temperature.

16. The apparatus of claim 15 wherein the means for determining the coefficient of thermal expansion is an electronic device.

17. The apparatus of claim 5 wherein the container is made of aluminum.

18. The apparatus of claim 5 wherein the container is selected from the group consisting of steel, stainless steel, alloys of steel, and combinations thereof.

19. The apparatus of claim 5 further comprising:
   a plurality of cavities in the container; and
   a pressure sensor for each of the plurality of cavities.

20. The apparatus of claim 19 wherein the geometric configuration for each cavity is different.

21. The apparatus of claim 5 wherein the cavities are cylindrical and have a height greater than the radius of the cavity.

22. An apparatus for determining a bulk material property of a polymer with temperature compensation comprising:
   a first container having a cavity adapted to hold an elastomeric material and which prevents radial expansion of said elastomeric material;
   means for applying pressure to an elastomeric material contained in the first container adapted to measure the pressure of the elastomeric material;
   a second container having a cavity adapted to hold the elastomeric material and which prevents radial expansion of said elastomeric material;
   a second pressure sensor in the second container adapted to measure the pressure of the elastomeric material; and
   means for determining a bulk material property of the elastomeric material (wherein the bulk material property is selected from the group consisting of Poisson's ratio and a ratio of shear modulus to bulk modulus) in communication with the first and second pressure sensors wherein the means for determining a bulk material property uses (A) the measured pressures from the first and second pressure sensors and (B) the applied pressure to determine the bulk material property.

* * * * *